United States Patent
Jain et al.

(12) 
(10) Patent No.: US 6,346,631 B1
(45) Date of Patent: Feb. 12, 2002

(54) PROCESS FOR THE PREPARATION OF ARTEETHERS FROM DIHYDROARTEMISININ

(75) Inventors: Dharam Chand Jain; Rajendra Singh Bhakuni; Sudhanshu Saxena; Sushil Kumar, all of Uttar Pradesh; Ram Asrey Vishwakarma, New Delhi, all of (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 09/535,513

(22) Filed: Mar. 24, 2000

(51) Int. Cl.$^7$ .................. C07D 321/02; C07D 321/10
(52) U.S. Cl. ........................ 549/348; 514/450
(58) Field of Search .......................... 549/348

(56) References Cited

U.S. PATENT DOCUMENTS 4,791,135 A * 12/1988 Lin et al. ............... 514/450
5,011,951 A * 4/1991 Buchs ..................... 549/348
5,171,676 A * 12/1992 Ziffer et al. .............. 435/124

OTHER PUBLICATIONS

Lin et al., "Antimalarial Activity of α–Alkylbenzylic Ethers," *J. Med. Chem.* 38:764–770 (1995).
Bhakuni et al., "An improved procedure for the synthesis of ethers of dihydroartemisinin," *Indian Journal of Chemistry* 34B: 529–530 (Jun. 1995).
El–Feraly et al., "A New Method for the Preparation of Arteether and its C–9 Epimer," *Journal of Natural Products* 55, 7:878–883 (Jul. 1992).
Brossi et al., Arteether, a New Antimalarial Drug: Synthesis and Antimalarial Properties, *J. Med. Chem.* 31: 645–650 (1988).

* cited by examiner

*Primary Examiner*—Alan L. Rotman

(57) ABSTRACT

The invention relates to an improved process for the preparation of arteether. The process comprises dissolving dihydroartemisinin in dry ethanol, adding a solid acid catalyst with trialkylorthoformate in the reaction mixture, stirring the reaction mixture at room temperature, adding $H_2O$ to the reaction mixture, extracting the reaction product with a non-polar organic solvent, and drying the solvent over anhydrous sodium sulphate and evaporating the solvent to obtain pure arteether.

7 Claims, No Drawings

PROCESS FOR THE PREPARATION OF ARTEETHERS FROM DIHYDROARTEMISININ

FIELD OF INVENTION

The present invention relates to an improved process for the preparation of arteether. Arteether is an ethyl ether derivative of dihydroartemisinin. The dihydroartemisinin is derived from artemisinin, which is a unique sesquiterpene lactone isolated from the plant *Artemisia annua*. Arteether prepared for the process of the invention is useful for the treatment of uncomplicated/severe complicated/cerebral and multi-drug resistant malaria.

BACKGROUND OF THE INVENTION

Approximately, 300–400 million people world wide now suffer from malaria, and each year 1–3 million (mostly children) die from this infectious disease. The rapidly spreading multi-drug resistance of parasite to standard quinoline based antimalarial drugs such as chloroquine and mefloquine complicates chemotherapy treatment of malarial patients. A new class of non-alkaloidal antimalarial compounds artemisinin (derived from *Artemisia annua*) and its semi-synthetic derivatives, artemether, arteether and artesunate as well as promising artelinic acid are increasingly being used for the treatment of uncomplicated/severe complicated/cerebral and multi-drug resistant malaria.

Arteether is a totally new drug introduced in India and has under gone extensive preclinical, animal, toxicological studies as well as clinical studies in Indian subjects as per drug regulatory requirements. Arteether is an ideal antimalarial drug especially for treating drug resistant and complicated *P. falciparum* malaria. Arteether show rapid schizontocidal action with quicker parasite clearance rate and short fever clearance time, virtually with no side effects and low recrudescence rate.

Brossi, et al (Brossi A; Vengopalan, B.; Dominguez Gerpe, L; Yeh, H. J. C.; Flipper-Anderson, J. L. Buchs, P; Luo, X. D.; Miehous, W and Peters, W. J. Med. Chem. 31, 646–649, 1988) report the isolation of arteether by dissolving dihydroartemisinin in a solvent mixture of benzene and ethanol by heating the solution at 45° C., followed by addition of $BF_3$-etherate and reaction mixture was refluxed at 70° C. for 1 hr. The reaction mixture was washed with 10% sodium acetate solution and extracted by dichloromethane, dried over anhydrous sodium sulphate followed by evaporation yielded α, β mixture of arteether and some side products. Chromatography of the reaction product was done to remove some impurities formed during the reaction.

EL-Feraly et al (F. EL-Feraly, M. A. Al-yahYa, K Y. Orabi, D. R. McPhail and A. T. McPhail J. Nat. Prod. 55, 878–883,1992) report the preparation of arteether by a process in which anhydrodihydroartemisinin, prepared from the artemisinin, was dissolved in absolute alcohol. The reaction mixture was stirred in presence of p-toluene sulphonic acid used as a catalyst. Upon workup, it yielded a mixture of β arteether and C-11 epimer in the ratio 3:1. In this process, only β arteether is obtained and separation of its C-11 epimer is difficult and preparation of anhydrodihydroartemisinin is a tedious process. The reaction took 22 hours to complete. The Lewis acid catalyst used in this reaction is required in large amount (60 mg acid catalyst by 100 mg anhydrodihydroartemisinin).

Another method is reported by Bhakuni et al. (Bhakuni R. S; Jain D. C and Sharma, R P., Indian J. Chemistry, 34B, 529–30 (1995). Arteether was prepared by dissolving dihydroartemisinin in alcohol and benzene mixture and then adding chlorotrimethylsilane as acid catalyst. The reaction was stirred for 2 hrs. at room temperature. The reaction mixture was washed with 10% sodium acetate solution and workup as usual method. The other products formed during the reaction were removed by column chromatography, to obtain pure arteether.

Another method is reported by Lin et al. (A. J Lin and R. E. Miller. J. Med. Chem. 38, 764–770 1995), in which the new ether derivatives were prepared by dissolving dihydroartemisinin in anhydrous ether and adding appropriate alcohol followed by boron trifluoride etherate. The reaction mixture was stirred at room temperature for 24 hrs. The yield of purified products ranged from 40–90%. Purification was achieved by the use of silica gel chromatography.

The above methods suffer from some disadvantages. Benzene is used as solvent, which on work up left a few non-volatile impurities in the reaction product. Also, the use of benzene as a solvent is not acceptable in Europe due to its carcinogenic nature. The minor products formed during the reaction require separation by column chromatography, thereby causing loss of arteether yield.

OBJECTIVES OF THE INVENTION

It is an object of the invention to provide an improved process for the preparation of arteether by replacing benzene as a solvent.

It is another object of the invention to obtain pure arteether without requiring chromatography to separate minor by-products.

It is a further object of the invention to replace the liquid acid catalyst used in the prior art by a solid acid catalyst.

It is a further object of the invention to provide a process the preparation of arteether wherein the quantity of solid acid catalyst required is also minimised.

It is another object of the invention to reduce the reaction time and temperature conditions for the isolation process.

It is another object of the invention to provide an improved process for the preparation of arteether which results in higher yield with 30:70 ratio of α-β-isomers of arteether in the reaction product.

It is another object of the invention to provide an improved process for the preparation of arteether from dihydroartemisinin that is cost effective and economical.

SUMMARY OF THE INVENTION

The present invention provides a process for the preparation of arteether from dihydroartemisinin, which comprises dissolution of dihydroartemisin in alcohol and adding a solid acid catalyst along with trialkylorthoformate in the reaction mixture, which produce higher yield of arteether, without chromatography. The solid acid catalyst can be reused in the process.

Accordingly, the present invention provides an improved process for the preparation of arteether, which comprises:

(a) dissolving dihydroartemisinin in dry ethanol;

(b) adding a solid acid catalyst with trialkylorthoformate in the reaction mixture;

(c) stirring the reaction mixture at room temperature for a period ranging from 1 to 10 hours;

(d) adding $H_2O$ to the reaction mixture and extracting the reaction product with a non-polar organic solvent, and (e) drying the solvent in step (d) above over anhydrous sodium sulphate and evaporating the solvent to obtain pure arteether.

In an embodiment of the present invention, the sold acid catalyst is selected from p-toluenesulphonic acid, anhydrous AlCl₃ and cation exchange resins.

In a further embodiment of the invention, the dihydroartemisinin and the solid acid catalyst are used in a ratio of 1–2:1 w/w.

In another embodiment of invention, the trialkylorthoformate is selected from triethylorthoformate, trimethylorthoformate and other trialkylorthoformate.

In a further embodiment of the invention, the dihydroartemisinin and the trialkylorthoformate are used in the ratio of 10–25:1.

In another embodiment of the invention, ethanol is used as a solvent and the reactant.

In another embodiment of the invention, the reaction product is stirred at a temperature ranging between 20–40° C. and the ratio of $\alpha$ and $\beta$ arteether isomers obtained in the reaction product is $\alpha{:}\beta$ arteether=20–30:80–70.

In another embodiment of the invention, the solid acid catalyst cation exchange resin can be regenerated and reused in the reaction.

DETAILED DESCRIPTION OF THE INVENTION

In the process of the invention, dihydroartemisinin is dissolved in absolute ethanol rather than benzene or anhydrous ether. In prior art processes, dihydroartemisinin was dissolved in the solvent benzene, which resulted in non-volatile impurities remaining in the product arteether after completion of reaction and work up. Benzene is also reported to be a carcinogenic in nature and is banned in some European countries. In the process of the invention, the ethanol used acts both as solvent and reactant.

The solid acid catalyst used in the process of the invention increases the purity of arteether. Prior art processes use liquid acid catalyst, which contain some impurities and are difficult to purify. The addition of reagent triethylorthoformate in the process of the invention reduces the quantity of acid catalyst required and the time of completion of the reaction at room temperature.

Another advantage of the reagent is that the reaction is completed at room temperature, without forming any side products whereas in the previous methods reaction mixture had to be heated up to 70° C. for 1–2 hrs resulting in the production of side products in the reaction.

As the reaction is carried under room temperature and no side products are formed, there is no need of chromatography for the purification of the product. This results in arteether being obtained in higher yield due to no loss of starting material in the formation of side products. Also the need for chromatography is avoided. The work up of reaction is simple as it comprises only extraction of reaction product with non-polar solvent and drying over sodium sulphate and evaporation under vacuum. The arteether is obtained in pure form and is not contaminated with the impurities of benzene and other solvents. The cation exchange resin used in the reaction as acid catalyst economises the preparation of reaction product as the resin is recovered by filtration of reaction product and can be reused. The pure arteether was obtained by drying and evaporation of organic solvent. The process of the invention provides pure and high yield of arteether. The two isomers of arteether obtained in the reaction are in the ratio of 30:70 (+5%).

The improvement in the process for the preparation of arteether from dihydroartemisinin comprises i), dissolution of dihydroartemisinin in ethanol, ii), stirring the solution for 10 min at room temperature iii), addition of triethylorthoformate and acid catalyst in the reaction mixture iv), followed by further stirring of the reaction mixture at room temperature v) addition of water and non polar solvent in the reaction mixture and finally, the organic solvent is dried over anhydrous sodium sulphate, evaporation of the reaction mixture yield the pure arteether.

The invention further provides a method for the preparation of different arteethers using different trialkylorthoformate and alcohols.

The details of the invention are provided in the following examples are given by way of illustration only and should not be construed to limit the scope of the present invention.

EXAMPLE-1
Use of p-Toulene Sulphonic Acid as Catalyst

Dihydroartemisinin (50 mg) was dissolved in dry ethanol (3 ml) In the reaction mixture ptoluene sulphonic acid (25 mg) and triethylorthoformate (2 ml) was added. After addition reaction mixture was stirred at 40° C. for 15 min. at oil bath. After cooling, 50 ml water was added in the reaction mixture. The reaction product was extracted with dichloromethane (30 ml×3). Total solvent obtained was dried over anhydrous sodium sulphate and evaporate the solvent under reduced pressure at 45° C. The yield of pure arteether obtained was 50 mg. The compound was characterised by IR, Mass, ¹H NMR.

EXAMPLE-2
Use of p-Toulene Sulphonic Acid as Catalyst

Dihydroartemisinin (50 mg) was dissolved in dry ethanol (3 ml). Add 2 ml of triethylorthoformate and (25 mg) of p-toluenesulphonic acid. The reaction mixture was stirred at room temperature (20° C.) for 30 min. 50 ml of water was added in the reaction mixture The reaction product was extracted by dichloromethane (30 mil×3). The dichloromethane extract was dried over anhydrous sodium sulphate and evaporation of solvent under vacuum at 40° C. and yielded the arteether (52 mg).

EXAMPLE-3
Use of Anhydrous Aluminium Chloride a Acid Catalyst

Dihydroartemisinin (50 mg) was dissolved in dry ethanol (3 ml). Add 2 ml of triethylorthoformate and anhydrous AlCl₃ (33 mg) was added in the reaction vessel. The reaction mixture was refluxed at 40° C. for 45 min over oil bath with constant stirring. After 45 mins of stirring the reaction product was worked up as mention in the example-3. The pure arteether yielded (45 mg).

EXAMPLE-4
Use of Trimethyl Orthoformate for the Preparation of Methyl Ether

Dihydroartemisinin (50 mg) was dissolved in dry methanol (3 ml). Add 2 ml of trimethylorthoformate and 25 mg of p-toluenesulphonic acid in the reaction. The reaction mixture was stirred at room temperature 30° C. for 30 min. The reaction was work up as shown in the example-1. The pure methyl ether yields (51 mg).

EXAMPLE-5
Use of Cation Exchange Resin as Acid Catalyst

Dihydroartemisinin (50 mg) was dissolved in 3 ml dry ethanol with stirring the solution for 10 min. at room temperature and add cation exchange resin (Dowex-50, 50 mg) and triethylorthoformate (4 ml) in the solution. The reaction mixture is stirred for 10 hrs at room temperature (30° C.). Water was added in the reaction mixture and filters the cation exchange resin. The reaction product was extracted by dichloromethane. The organic layer was separated, dried over anhydrous sodium sulphate and evaporated under vacuum to yield pure arteether (50 mg).

The Advantage of the Process of the Present Invention

1. The yield of arteether obtained in quantitative amount (more than 95%.)
2. The reaction is carried out at room temperature (20–40° C.) where as in $BF_3$ etherate procedure the reaction is carried at 70° C., which gives side reaction products.
3. The purification of the product through chromatography is avoided in the present process because of no side products formed during reaction.
4. The solvent benzene is used in the previous process, which is carcinogenic in nature, and contains some non-volatile impurities, which is to be avoided in this process.
5. Solid acid catalyst was used in this process in very small amount in comparison to previous methods.
6. Cation exchange resin used as an acid catalyst is advantageous as it can be removed by simple filtration from the reaction mixture and reused repeatedly.
7. Cation exchange resins do not form any stable complex with reagent or product.
8. The acid catalyst used in the previous process are low boiling solvents ($BF_3$ etherate Chlorotrimethylsilane) and removal of moisture and purification from these liquid can be a difficult task.

We claim:

1. A process for the preparation of arteether, which comprises:
   (a) dissolving dihydroartemisinin in dry ethanol;
   (b) adding a solid acid catalyst with trialkylorthoformate in the reaction mixture;
   (c) stirring the reaction mixture at room temperature for a period ranging between 1 to 10 hours;
   (d) adding $H_2O$ to the reaction mixture and extracting a reaction product with a non-polar organic solvent, and
   (e) drying the solvent in step (d) over anhydrous sodium sulphate and evaporating the solvent to obtain pure arteether.

2. A process as claimed in claim 1 wherein the dihydroartemisinin and the solid acid catalyst are used in a ratio of 1–2:1 w/w.

3. A process as claimed in claim 1 wherein the trialkylorthoformate is a member selected from the group consisting of triethylorthoformate and trimethylorthoformate.

4. A process as claimed in claim 1 wherein the dihydroartemisinin and the trialkylorthoformate are used in the ratio of 10–25:1.

5. A process as claimed in claim 1 wherein ethanol is used as a solvent and as a reactant.

6. A process as claimed in claim 1 wherein the reaction product is stirred at a temperature ranging between 20–40° C. and the ratio of $\alpha$ and $\beta$ arteether isomers obtained in the reaction product is $\alpha:\beta$ arteether=20–30:80–70%.

7. A process as claimed in claim 1 wherein the solid acid catalyst is a cation exchange resin and the cation exchange resin is regenerated and reused in the reaction.

* * * * *